United States Patent [19]

Fujino et al.

[11] 4,111,924

[45] Sep. 5, 1978

[54] METHOD FOR REMOVAL OF THIOL-PROTECTING GROUPS

[75] Inventors: Masahiko Fujino, Takarazuka; Osamu Nishimura, Toyonaka; Chieko Kitada, Sakai, all of Japan

[73] Assignee: Takeda Chemical Industries, Ltd., Osaka, Japan

[21] Appl. No.: 805,900

[22] Filed: Jun. 13, 1977

[30] Foreign Application Priority Data

Jun. 28, 1976 [JP] Japan .................................. 51-76676

[51] Int. Cl.$^2$ ....................... C07C 103/52; C07G 7/00
[52] U.S. Cl. ...................... 260/112.5 R; 260/112.5 S; 260/112.5 T
[58] Field of Search .................. 260/112.5 R, 112.5 S, 260/112.5 T, 430

[56] References Cited

U.S. PATENT DOCUMENTS

| | | | |
|---|---|---|---|
| 3,560,521 | 2/1971 | Milkowski et al. | 260/112.5 R |
| 3,917,578 | 11/1975 | Immer et al. | 260/112.5 R |

*Primary Examiner*—Delbert R. Phillips
*Assistant Examiner*—B. Hazel
*Attorney, Agent, or Firm*—Burgess, Ryan and Wayne

[57] ABSTRACT

A novel method for removal of protective group(s) from an amino acid or peptide having thiol group(s) protected with p-methoxybenzyl, 1-adamantyl or t-butyl group by treating the protected amino acid or peptide with the mercuric salt of acetic acid or halogenoacetic acid, the removal being effected selectively and very smoothly in a good yield under extremely mild conditions without giving any undesirable influence upon other functional or protective group(s).

3 Claims, No Drawings

METHOD FOR REMOVAL OF THIOL-PROTECTING GROUPS

This invention relates to a novel and useful method for removal of thiol-protecting groups.

More specifically, the present invention is directed to a method for removal of protective group(s) from an amino acid or peptide having thiol group(s) protected with p-methoxybenzyl, 1-adamantyl or t-butyl.

Generally, in organic reactions it is often necessary to protect and, then, regenerate a thiol group. Especially in peptide synthesis, protection and regeneration of thiol groups is quite important.

Among procedures of protecting a thiol group and, then, removing the protective group, the most widely available procedures are the procedure of protecting it with a benzyl group and, then, removing this protective group with metallic sodium in liquid ammonia and of protecting the thiol with p-methoxybenzyl and then removing the latter with refluxing trifluoroacetic acid or anhydrous hydrogen fluoride ["J. Biol. Chem. Vol. 108, 753–761 (1965)", "Bull. Chem. Soc. Japan, Vol. 37, No. 3, 433–434 (1964)", and "Bull. Chem. Soc. Japan, Vol. 40, 2164–2167 (1967)"].

However, because the conditions employed in the removal of such protective groups are somewhat drastic, there are cases in which it is found to be impossible to selectively remove the thiol-protecting group with the other functional groups and protective groups being kept intact.

Because t-butyl and 1-adamantyl groups may be easily introduced to the thiol group, attempts have been made to utilize them as protective groups for thiol, only to find, however, that these protective groups are very difficult to remove subsequently ["J. A. C. S. Vol. 85, 201–207 (1963)"]. Thus, no effective procedure for removing such protective groups has been known.

Under these circumstances we sought a new method of regenerating a thiol group protected by p-methoxybenzyl, 1-adamantyl or t-butyl and have discovered that such protective groups may be removed with extreme ease and in good yield by treating the substrate under very mild conditions, i.e. with a mercuric salt of a carboxylic acid of the formula $CX_3COOH$ (I) wherein X is hydrogen, chlorine or fluorine.

Developed as a sequel of the above finding, this invention relates to a method for removal of a protective group from an amino acid or peptide having thiol group(s) protected with p-methoxybenzyl, 1-adamantyl or t-butyl characterized in that the protected amino acid or peptide is treated with a mercuric salt of a carboxylic acid (I).

In accordance with the invention, an amino acid or peptide having a thiol group or thiol groups protected with p-methoxybenzyl, 1-adamantyl or t-butyl is treated with a mercuric salt of a carboxylic acid (I).

The present method is applicable to any amino acids having thiol group(s) protected with the protective group(s) and those amino acids may be exemplified by cysteine or homocysteine. The present method is also applicable to any peptides having thiol group(s) protected with the protective group(s).

These peptides may be those having cysteine, homocysteine or any other thiol-containing amino acid residue as one or more moieties constituting the same, whose thiol group(s) are protected with the protecting group(s), and a typical example of those peptides is glutathione. The present method is further applicable for preparation of amino acids or peptides having disulfide linkage(s) (e.g. cystine, oxytocin, vasopressin, somatostatin, insulin, calcitonine, trypsin inhibitor, ribonuclease or lysozyme). The peptides employable in the present method may have moieties other than amino acid residues as long as the peptides have the protected thiol group(s).

As examples of said mercuric salt of carboxylic acid may be mentioned the mercuric salts of acetic acid, dichloroacetic acid, trichloroacetic acid, trifluoroacetic acid, the mercuric salts of acetic acid and trifluoroacetic acid being particularly preferred. Based on the amino acid or peptide, such a mercuric salt may be used in a proportion of, for example, 1 to about 4 molar equivalents.

In the practice of this invention, the direct addition of such a mercuric salt to the reaction system may be replaced by the addition of materials which are able to yield such a mercuric salt in the reaction system. For example, mercuric oxide may be dissolved in said carboxylic acid (I) so that the resultant mercuric salt may be utilized for the purposes of this invention.

The method of this invention may normally be practiced in the presence of a solvent. The solvent may for example be a carboxylic acid (I) (e.g. acetic acid, dichloroacetic acid, trichloroacetic acid or trifluoroacetic acid or a mixture of such an acid) with water. It is also possible to select one, which is able to dissolve the desired compound with comparative ease and is suited to the contemplated reaction, from among such other solvents as water, alcohols (e.g. methanol, ethanol, propanol, butanol, and mixtures thereof with water), tetrahydrofuran, dioxane, dimethylformamide, chloroform, acetonitrile, formic acid and mixtures thereof with water, for instance. The method of this invention may be practiced at an appropriate temperature, for example in the range of about $-20°$ C. to about $100°$ C., preferably about $0°$ C. to about $80°$ C.

While the treating time according to this invention depends upon such factors as the types and amounts of the amino acid or peptide, solvent and mercuric salt employed, it is in many cases sufficient to conduct the treatment for about 30 seconds to 12 hours.

While the thiol-protecting group, i.e. p-methoxybenzyl, 1-adamantyl, t-butyl, may thus be removed by the method of this invention, the amino acid or peptide may be in the form of a mercaptide in certain cases and the free thiol group may be regenerated by a procedure known per se. For example, the mercaptide is dissolved or suspended in water, an aqueous solvent or an organic solvent (e.g. formic acid, acetic acid, dimethylformamide, tetrahydrofuran) and treated with mercapto compound (e.g. hydrogen sulfide, mercaptoethanol, thioglycolic acid, sodium sulfide, ammonium sulfide), whereby the free thiol group is regenerated.

The method of this invention has the following utility features.

(1) The removal of protective groups is accomplished under extremely mild conditions.

(2) The protective groups may be removed in good yield.

(3) The procedure and after-treatment are easy and simple.

(4) The protective group on thiol may be selectively removed with other functional and protective groups being kept intact.

The following are exemplary processes for the production of the amino acid or peptide with protected-thiol group(s) as reference examples and exemplary procedures for removing the protective groups as working examples.

Throughout this specification, when abbreviations are used to denote amino acids, peptides, protective groups, etc., the nomenclature prescribed by IUPAC IUB and the trivial names commonly used in this particular field will be employed. Whenever any amino acid has D- and L-configurations, any reference to such an acid indicates the L-form thereof unless the D-form is specifically mentioned.

REFERENCE EXAMPLE 1

Production of S-1-adamantyl-L-cysteine (H-Cys-OH)

In 120 ml of trifluoroacetic acid is dissolved 12.1 g of L-cysteine, followed by addition of 15.2 g of 1-adamantanol. The mixture is stirred at room temperature for 12 hours. The trifluoroacetic acid is distilled off under reduced pressure. The oily residue is dissolved in 200 ml of water and cooled with ice. The solution is then brought to pH 6.0 with concentrated aqueous ammonia, whereupon crystals separate out. The crystals are collected by filtration, rinsed with water, ethanol and ether, and recrystallized from water.

Yield: 23.0 g; m.p.: 227.0°–228.0° C. (decomp.)
$[\alpha]_D^{26} -14.5°(c=0.51,$ glacial acetic acid)
Elemental analysis: Calcd. for $C_{13}H_{22}O_2NS$: C, 60.90; H, 8.65; N, 5.46; S, 12.51. Found C, 59.51; H, 8.16; N, 5.41; S, 12.33.

REFERENCE EXAMPLE 2

Production of S-t-butyl-L-cysteine (H—Cys—OH)

Using L-cysteine and t-butanol, the same procedure as Reference Example 1 is followed to produce the above compound. m.p.: 244.0°–245.0° C.
$[\alpha]_D^{26} -15.4°(c=0.57;$ glacial acetic acid)
Elemental analysis: Calcd. for $C_7H_{15}O_2NS$: C, 45.13; H, 8.65; N, 7.52; S, 17.22. Found C, 45.11; H, 8.32; N, 7.47; S, 17.77.

REFERENCE EXAMPLE 3

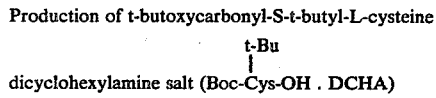

Production of t-butoxycarbonyl-S-t-butyl-L-cysteine dicyclohexylamine salt (Boc-Cys-OH . DCHA)

In the conventional manner, the

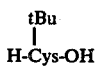

H-Cys-OH obtained in Reference Example 2 is t-butoxycarbonylated with t-butyl-S-4, 6-dimethylpyrimidine-2-ylthiolcarbonate and, then, crystallized as the dicyclohexylamine salt. Yield: 90%, m.p.: 181.0°–182.5° C.
$[\alpha]_D^{25} +7.4°$ $(c=0.83,$ methanol)
Elemental analysis: Calcd. for $C_{24}H_{46}O_4N_2S$: C, 62.93; H, 10.10; N, 6.10; S, 6.99. Found C, 62.92; H, 10.36; N, 5.95; S, 7.05.

t-Butoxycarbonyl-S-1-adamantyl-L-cysteine dicyclohexylamine salt

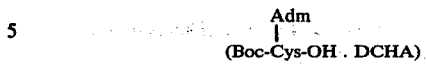

is produced in the same manner as above.
Yield: 71.4%; m.p.: 173.0°–174.0° C.;
$[\alpha]_D^{25} +5.8°(c=0.55,$ methanol)
Elemental analysis: Calcd. for $C_{30}H_{53}O_4N_2S$: C, 67.00; H, 9.93; N, 5.21; S, 5.96. Found C, 67.09; H, 9.88; N, 5.08; S, 5.85.

The t-butoxycarbonyl-S-p-methoxybenzyl-L-cysteine

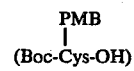

(Boc-Cys-OH)

used is a commercial product.

REFERENCE EXAMPLE 4

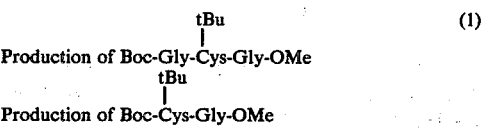

In 30 ml of chloroform is dissolved 3.0 g of glycine methyl ester hydrochloride and, under ice-cooling, 3.36 ml of triethylamine is added. To this mixture is added the N-hydroxy-5-norbornene-2,3-dicarboximide (HONB) ester of

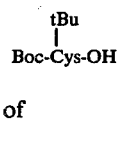

(prepared from 9.2 g of

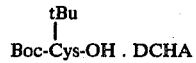

and 3.6 g of HONB in dioxane with 4.1 g of dicyclohexylcarbodiimide as a condensing agent) and the mixture is stirred at room temperature for 12 hours. The chloroform is distilled off under reduced pressure and the oily residue is dissolved in 24–150 ml of acetic acid and washed with a 4% aqueous solution of sodium hydrogen carbonate, a saturated aqueous solution of citric acid and, finally, water. The ethyl acetate is then evaporated off and the residue is crystallized by addition of water.

Yield: 5.9 g.; m.p.: 73.0°–75.0° C.
$[\alpha]_D^{26} -17.9°(c=0.56,$ dimethylformamide)
Elemental analysis: Calcd. for $C_{15}H_{28}O_5N_2S$: C, 51.70; H, 8.10; N, 8.04; S, 9.20. Found C, 51.70; H, 8.12; N, 8.05; S, 9.14.

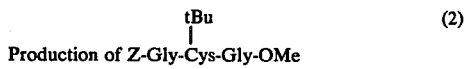

In 30 ml of trifluoroacetic acid is dissolved 5.23 g of

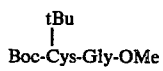
Boc-Cys-Gly-OMe and the solution is shaken at room temperature for 15 minutes. The trifluoroacetic acid is evaporated off under reduced pressure and the residue is dried well. It is then dissolved in 30 ml of dimethylformamide and, under ice-cooling, 7.0 ml of triethylamine is added. Following addition of 5.8 g of Z-Gly-ONB, the mixture is stirred for 48 hours. The dimethylformamide is evaporated off under reduced pressure and the residue is dissolved in ethyl acetate. The solution is washed with a 4% aqueous solution of sodium hydrogen carbonate, 1N-hydrochloric acid and water, followed by concentration to dryness under reduced pressure. To the residue is added petroleum ether and the mixture is allowed to stand, whereupon crystals separate out. The crystals are collected by filtration.

Yield: 6.1 g.; m.p.: undeterminable because it is liquid at room temperature.

$[\alpha]_D^{26} -11.4°(c=0.46,$ dimethylformamide)

Elemental analysis: Calcd. for $C_{20}H_{29}O_6N_3S$: C, 54.65; H, 6.65; N, 9.56; S, 7.30. Found C, 55.11; H, 6.60; N, 9.48; S, 6.55.

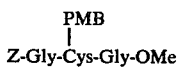
Z-Gly-Cys-Gly-OMe is also produced in the same manner as above.
m.p.: 90.0°–95.0° C.;
$[\alpha]_D^{27} -23.1°(c=0.55;$ dimethylformamide)

Elemental analysis: Calcd. for $C_{24}H_{29}O_7N_3S$: C, 57.20; H, 5.80; N, 8.34; S, 6.37. Found C, 57.60; H, 5.81; N, 8.23; S, 6.36.

EXAMPLE 1

Recovery of cysteine from S-protected cysteine (1) S-protected cysteine (1mM) is dissolved in 10 ml of trifluoroacetic acid, followed by addition of 0.2 ml of anisole. The mixture is cooled to 0° C. and 319 mg (1mM) of $Hg(CH_3COO)_2$ is added. The mixture is stirred at 0° C. for 15 minutes. The trifluoroacetic acid is evaporated off under reduced pressure over a period of 5 minutes and 40 ml of water is added to the residue. The mixture is washed once with ether. Hydrogensulfide gas is bubbled into this solution for 30 minutes and the resultant HgS is filtered off, followed by concentration of the filtrate. This residue is dissolved in small amount of water, followed by evaporation of water to remove the excess of the acid. This procedure is repeated three times and the final residue is analyzed by an amino acid analyzer. The results are shown in the following table. S-Benzyl group is quite stable under the above conditions.

| S-protected amino acid | tBu<br>\|<br>H-Cys-OH | Adm<br>\|<br>H-Cys-OH | PMB<br>\|<br>H-Cys-OH |
|---|---|---|---|
| % Recovery of cysteine | 99.8% | 102.0% | 100.8% |

No removal of protective groups takes place when the above reaction is conducted using the acetate of Ag, Cu, Zn, Ni or Pb instead of $Hg(CH_3COO)_2$.

(2) S-protected cysteine (1mM) is dissolved in 10 ml of 80% formic acid or 80% acetic acid, followed by addition of 0.2 ml of anisole. At room temperature, 319 mg (1mM) of $Hg(CH_3COO)_2$ is added and the mixture is stirred for 1 hour. The reaction mixture is treated and analyzed in the same manner as (1).

The results are set forth in the following table.

| Solvent | S-protected amino acid<br>PMB<br>\|<br>H-Cys-OH | tBu<br>\|<br>H-Cys-OH | Adm<br>\|<br>H-Cys-OH |
|---|---|---|---|
| 80% formic acid | 85.0% | 86.0% | 80.0% |
| 80% acetic acid | 73.0% | 48.0% | — |

(3) S-protected cysteine (1mM) is dissolved in 20 ml of 80% acetic acid, followed by addition of 0.2 ml of anisole and, then, 512 mg (1.2mM) of $Hg(CF_3COO)_2$. The mixture is stirred at room temperature for 1 hour.

The reaction mixture is then treated and analyzed in the same manner as (1).

The results are shown below.

| S-protected amino acid | PMB<br>\|<br>H-Cys-OH | tBu<br>\|<br>H-Cys-OH |
|---|---|---|
| % Recovery of cysteine | 94.0% | 92.0% |

When a solution of $Hg(CCl_3COO)_2$, instead of $Hg(CF_3COO)_2$, is used, the percent recovery of cysteine from

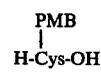
H-Cys-OH is 96.0%.

EXAMPLE 2

Production of Z-Gly-Cys-Gly-OMe

From Z-Gly-Cys-Gly-OMe: (1)

PMB
|
From Z-Gly-Cys-Gly-OMe:

In 45 ml of cold trifluoroacetic acid is dissolved 3.02 g of

PMB
|
Z-Gly-Cys-Gly-OMe, followed by addition of 1.5 ml of anisole. Following addition of 1.91 g of $Hg(CH_3COO)_2$ at 0° C., the mixture is stirred for 15 minutes. The trifluoroacetic acid is distilled off under reduced pressure and ether is added to the residue. The resultant precipitate is collected by filtration.

Yield: 4.1 g.

Elemental analysis: Calcd. for $C_{18}H_{20}O_8N_3SF_3Hg$: C, 31.06; H, 2.90; N, 6.04; S, 4.61; Hg, 28.82; F. 8.19. Found C, 31.02; H, 2.87; N, 6.18; S, 4.60; Hg, 28.68; F, 8.18.

In 30 ml of dimethylformamide is dissolved 2.0 g of the above mercaptide, and $H_2S$ gas is bubbled into the solution for 80 minutes. The resultant HgS is removed by filtration with Celite as a filter aid and the filtrate is concentrated to dryness under reduced pressure. To the crystalline residue is added water and the crystals are recovered by filtration and recrystallized from methanol and water.

Yield: 1.1 g (100%); m.p.: 130°-132° C.
$[\alpha]_D^{26} - 5.7°$ (c=0.57; dimethylformamide)
Elemental analysis: Calcd. for $C_{16}H_{21}O_6N_3S$: C, 50.12; H, 5.52; N, 10.96; S, 8.36. Found C, 49.61; H, 5.18; N, 10.97; S, 8.44.

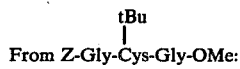

From Z-Gly-Cys-Gly-OMe:

Treatment of

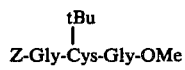

Z-Gly-Cys-Gly-OMe in the same manner as (1) gives the mercaptide and Z-Gly-Cys-Gly-OMe in the yields of 84.2% and 84.5%, respectively.

In melting point and $[\alpha]_D$, this compound is identical with the compound obtained in (1).

Elemental analysis: Calcd. C, 50.12; H, 5.52; N, 10.96; S, 8.36. Found C, 50.13; H, 5.61; N, 10.77; S, 8.27.

(3) The table below shows the yields of Z-Gly-Cys-Gly-OMe crystals as produced by the treatment of

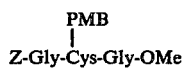

with $Hg(CF_3COO)_2$ in 80% acetic acid.

In 20 ml of 80% acetic acid is dissolved 1 mM of

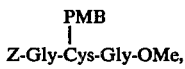

Z-Gly-Cys-Gly-OMe, followed by the addition of 512 mg (1.2 mM) or 853 mg (2.0 mM) of $Hg(CF_3COO)_2$. The mixture is stirred at room temperature for 60 minutes. Following addition of 40 ml of 80% acetic acid, $H_2S$ gas is bubbled into the mixture over 20 minutes. The HgS is filtered off and the filtrate is concentrated to dryness under reduced pressure. To the residue is added water and the resultant crystals are collected by filtration and recrystallized from ethyl acetate.

| $Hg(CF_3COO)_2$ | 1.2 molar equiv. | 2.0 molar equiv. |
|---|---|---|
| Yield | 83.9% | 76.5% |

When the above reaction procedure is carried out by using 1.2 molar equivalents of $Hg(CCl_3COO)_2$ in lieu of $Hg(CF_3COO)_2$, the yield of Z-Gly-Cys-Gly-OMe is 74.9%.

EXAMPLE 3

Production of bis-t-butoxycarbonyl-L-cystine

In 200 ml of 80% aqueous methanol is dissolved 3.41 g of

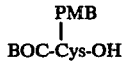

BOC-Cys-OH and, following addition of 5.12 g of $Hg(CF_3COO)_2$, the solution is stirred at room temperature for 2 hours. Then, following addition of 100 ml of 80% aqueous methanol, $H_2S$ gas is bubbled into the reaction mixture for 30 minutes. The resultant HgS is filtered off and the filtrate is concentrated under reduced pressure to half its initial volume. To the residue is added 4.2 g of sodium hydrogen carbonate and the mixture is further concentrated under reduced pressure. After the methanol has been removed, 100 ml of water is added to the residue, and oxidation is carried out by the introduction of air over a period of 40 hours. The mixture is acidified with citric acid and the resultant oil is extracted twice with 150 ml portions of ethyl acetate. The ethyl acetate is distilled off, and the residue is crystallized by addition of petroleum ether and is collected by filtration. The crystalline product is recrystallized from ethyl acetate.

Yield: 1.85 g., m.p.: 149.0°-150.0° C. (decomp.)
$[\alpha]_D^{20} - 136.4°$ (c=1.84, in methanol)
Elemental analysis: Calcd. for $C_{16}H_{28}O_8N_2S_2$: C, 43.62; H, 6.48; N, 6.36; S, 14.55. Found C, 43.72; H, 6.34; N, 6.24; S, 14.25.

EXAMPLE 4

Production of oxytocin (1) Production of Boc-Cts(PMB)-Tyr-Ile-Gln-Asn-Cys(PMB)-Pro-Leu-Gly-resin Boc-Gly-resin (Gly content: 2.2 mM) is placed in the reaction vessel of a Shimadzu automatic peptide synthesizer APS-800 and the following procedure is carried out in sequence.

(1) Washing with dichloromethane (2 min. × 3 times)
(2) 50% trifluoroacetic acid-dichloromethane (10 min. × twice)
(3) Washing with dichloromethane (2 min. × 3 times)
(4) Washing with ethanol (2 min. × 3 times)
(5) Washing with chloroform (2 min. × 3 times)
(6) 10% triethylamine-chloroform (2 min. & 10 min., once each)
(7) Washing with chloroform (2 min. × 3 times)
(8) The condensation reaction with 6.6 mM of BOC-amino acid symmetric anhydride (60 min.) or 6.6 mM of BOC-amino acid p-nitrophenyl ester (12 hours for BOC-Asn, Boc-Gln or Boc-Tyr)
(9) Washing with dichloromethane (2 min. × 3 times)
(10) Acetylation of the unreacted amino group (4.5% acetic anhydride-dichloromethane)
(11) Washing with dichloromethane (2 min. × 3 times)

After all the reaction cycles have been completed, the product is washed with acetic acid, dimethylformamide and methanol in that order and dried. Yield: 13.15 g (2) Production of Boc-Cys(PMB)-Tyr-Ile-Gln-Asn-Cys(PMB)-Pro-Leu-Gly-NH$_2$ In 70 ml of methanol containing 15.5% of ammonia is suspended 12.6 g of the resin obtained in (1) and the suspension is stirred at room temperature for 46 hours.

The resin is filtered off and washed twice with 20 ml of dimethylformamide. The filtrate and washings are pooled and concentrated to dryness under reduced pressure. To the residue is added 50 ml of ether and the resultant powder is collected by filtration and dried. Yield: 2.86 g. This product is purified by repeated reprecipitation from hot methanol, aqueous ethanol and dimethylformamide-ethanol.

Yield: 1.0 g.

This powder is developed on a 2.8 × 4.0 cm column of silica gel (solvent system: chloroform-methanol-water-pyridine-acetic acid = 1085 : 150 : 25 : 63 : 84).

The fractions rich in the desired compound are pooled and concentrated to dryness.

Yield: 768 mg.

$[\alpha]_D^{21} -39.1°$ (c=0.47, in dimethylformamide)

Elemental analysis: Calcd. for $C_{66}H_{98}O_{16}N_{12}S_2 \cdot CH_3COOH \cdot H_2O$: C, 55.52; H, 6.92; N, 11.78; S, 4.49. Found C, 55.24; H, 7.00; N, 11.92; S, 4.43.

(3) Production of oxytocin

In 1 ml of trifluoroacetic acid is dissolved 125 mg of the powder produced in (2) together with 0.22 ml of anisole, followed by the addition of 127 mg of $Hg(CH_3COO)_2$. The mixture is allowed to stand at room temperature for 30 minutes. Following addition of 30 ml of ether, the resultant precipitate is collected by filtration (173 mg). This precipitate is dissolved in 3 ml of 50% aqueous acetic acid and, following addition of 0.31 ml of 2-mercaptoethanol, the resultant precipitate is filtered off. The filtrate is concentrated to dryness under reduced pressure. The residue is dissolved in 1 ml of 50% aqueous acetic acid and the solution is passed into a column (2.2. × 92.5 cm) of Sephadex G-15, elution being carried out with 50% acetic acid. The fractions 149 to 188 ml are pooled and lyophilized (85 mg).

The lyophilizate is dissolved in 150 ml of 0.1% aqueous acetic acid and after the solution is adjusted to pH 7.3 with 1N-aqueous ammonia, air is bubbled into the solution. After 4.5 hours, the solution is adjusted to pH 3.5 and lyophilized (76 mg). The lyophilizate is developed on a column similar to that mentioned above. The fractions from 154 to 188 ml are collected and lyophilized to give 50 mg of oxytocin.

$[\alpha]_D^{22} -24.6°$ (c=0.47, 1N-aqueous solution of acetic acid)

Amino acid analysis: Asp 1.03, Glu 1.13, Pro 1.06, Gly 1.00, Cys 1.97, Ile 1.03, Leu 1.03, Tyr 0.90

Thin-layer chromatography: Rf(n-butanol-acetic acid-water=3:1:1)=0.44; Rf(n-butanol-ethyl acetate-acetic acid-water=1:1:1:1)=0.66; (a single spot each).

EXAMPLE 5

Production of Somatostatin (1) Synthesis of H-Cys-O$^t$Bu . L-tartrate with PMB group on Cys To a suspension of 4.82 g (0.02 M) of H-Cys-OH (with PMB on side chain)

in 150 ml of dioxane is added dropwise 4.8 ml of concentrated sulfuric acid under stirring at room temperature. Into the mixture is bubbled 75 ml of isobutylene under ice-cooling. The mixture is tightly sealed and left standing at room temperature for 12 hours. The mixture is poured on to 300 ml of 1N solution of sodium hydroxide and extracted three times with ether. The ether layer is dried over anhydrous sodium sulfate and distilled off under reduced pressure. The oily residue is dissolved in 50 ml of ether, followed by addition of 3 ml of 6.69N hydrochloric acid-dioxane. The resulting crystals are collected by filtration and recrystallized from ethyl acetate. Yield: 2.4 g.

In ether is suspended 1.99 g of the crystals and 10 ml of 1N solution of sodium hydroxide is added. The mixture is shaken well enough to become a solution and extracted twice with ether. The ether solution is combined, dried and distilled under reduced pressure. The oily residue is dissolved in ethanol. In the solution is dissolved 900 mg of L-tartaric acid and the solution is left standing for a while. Resulting crystals are collected by filtration and recrystallized twice from ethanol.

Yield: 2.3 g m.p. 100.0°–102.0° C.

$[\alpha]_D^{27} -3.2°$ (c=0.53, dimethylformamide)

Elemental analysis: Calcd. for $C_{15}H_{23}O_3NS \cdot C_4H_6O_6 \cdot 1/2H_2O$: C, 49.99; H, 6.62; N, 3.07; S, 7.02. Found C, 49.85; H, 6.74; N, 2.98; S, 6.68.

(2) Synthesis of Z-Thr-Ser-OMe

In 50 ml of dimethylformamide is dissolved 6.22 g (0.04 M) of H-Ser-OMe.HCl, followed by addition of triethylamine under ice-cooling. Resulting salt is removed by filtration and 16.6 g (0.04 M) of Z-Thr-ONB is added to the filtrate. After the mixture is stirred at room temperature for 12 hours, the insolubles are removed by filtration and the filtrate is concentrated in vacuo. The oily residue is dissolved in ethyl acetate and saturated with NaCl and washed with 1 N HCl and 5% NaHCO$_3$. After being dried, the ethyl acetate is distilled off and resulting crystals are collected.

Yield: 10.6 g (74.5%) m.p. 133.0°–135.0° C.

$[\alpha]_D^{23} +10.1°$ (c=0.86, dimethylformamide)

Elemental analysis: Calcd. for $C_{16}H_{22}O_7N_2$: C, 54.23; H, 6.26; N, 7.91. Found C, 54.44; H, 6.33; N, 7.84.

(3) Synthesis of Z-Phe-Thr-Ser-OMe

In 100 ml of methanol is dissolved 9.91 g (0.028 M) of Z-Thr-Ser-OMe, followed by addition of 6.3 ml of 6.69 N HCl-dioxane. The mixture is subjected to catalytic reduction in the presence of palladium black in a conventional manner. The catalyst is removed by filtration and the filtrate is concentrated. The residue is dissolved in 50 ml of dimethylformamide and the solution is neutralized with 4.31 ml of triethylamine, followed by filtration. To the filtrate is added Z-Phe-ONB, which is prepared from 8.38 g (0.028 M) of Z-Phe-OH, 6.0 g (0.034 M) of HONB and 5.78 g (0.028 M) of dicyclohexylcarbodiimide, and the mixture is stirred at room temperature for 12 hours. The solvent is distilled off in vacuo, and the residue is dissolved in ethyl acetate, followed by washing and drying in a conventional manner. Evaporation of the solvent separates out crystals. After being cooled, the crystals are collected by filtration.

Yield: 11.0 g (80.0%). m.p.: 180.0°–182.0° C.

$[\alpha]_D^{23} -3.8°$ (c=0.67, dimethylformamide)

Elemental analysis: Calcd. for $C_{25}H_{31}O_8N_3 \cdot 1/2H_2O$. C, 58.81; H, 6.12; N, 8.23. Found C, 58.80; H, 6.25; N, 8.26.

(4) Synthesis of Z(NO$_2$)-Thr-OH.DCHA

The compound is prepared by the conventional procedure [F.H. Carpenter, D.T. Gish, J. Amer. Chem. Soc., 74, 3818 (1952)] with NaHCO$_3$ as a base.

Yield: 50.0% m.p.: 186.0°–188.0° C.

$[\alpha]_D^{23} +14.9°$ (c=0.77, dimethylformamide)

Elemental analysis: Calcd. for $C_{12}H_{14}N_2O_7 \cdot C_{12}H_{23}N$: C, 60.11; H, 7.78; N, 8.76. Found C, 60.14; H, 7.83; N, 8.80.

(5) Synthesis of Z(NO₂)-Thr-Phe-Thr-Ser-OMe

In a conventional procedure, 11.0 g (0.022 M) of Z-Phe-Thr-Ser-OMe is catalytically reduced into H-Phe-Thr-Ser-OMe in methanol. To this is added a tetrahydrofuran solution of Z(NO₂)-Thr-ONB which is prepared from 10.6 g (0.022 M) of Z(NO₂)-Thr-OH.DCHA, 3.94 g (0.022 M) of HONB and 4.54 g (0.022 M) of dicyclohexylcarbodiimide. The mixture is stirred at room temperature for 12 hours. The solvent is distilled off, followed by addition of water. Resulting crystals are collected by filtration and recrystallized from methanol.

Yield: 12.8 g (90.1%). m.p.: 194.0°–196.0° C.
$[\alpha]_D^{23} -0.7°$ (c=0.72, dimethylformamide)
Elemental analysis: Calcd. for $C_{29}H_{37}O_{12}N_5$: C, 53.78; H, 5.76; N, 10.81. Found C, 53.80; H, 5.85; N, 10.75.

(6) Synthesis of Z(NO₂)-Thr-Phe-Thr-Ser-NHNH₂

In 100 ml of dimethylformamide is dissolved 12.3 g (0.019 M) of Z(NO₂)-Thr-Phe-Thr-Ser-OMe, followed by addition of 100 ml of methanol and further addition of 9.5 ml (0.19 M) of hydrazine hydrate. The mixture is left standing at room temperature for 48 hours and cooled with ice. Resulting crystals are collected by filtration and recrystallized from methanol.

Yield: 11.4 g (92.7%). m.p.: 229.0°–232.0° C. (decomp.)
$[\alpha]_D^{23} +3.2°$ (c=0.44, dimethylformamide)
Elemental analysis: Calcd. for $C_{28}H_{37}O_{11}N_7 \cdot H_2O$: C, 50.52; H, 5.91; N, 14.81. Found C, 50.89; H, 5.92; N, 14.90.

$$\text{Synthesis of Z(NO}_2\text{)-Thr-Phe-Thr-Ser-Cys-O}^t\text{Bu} \overset{\text{PMB}}{|} \quad (7)$$

In 50 ml of dimethylformamide is dissolved 3.24 g (0.005 M) of Z(NO₂)-Thr-Phe-Thr-Ser-NHNH₂. While the solution is cooled to −20° C., 3.1 ml of 6.51 N HCl-dioxane is added and 0.81 ml (0.006 M) isoamylnitrite is added dropwise. After the minutes, the mixture is further cooled to −50° C. and neutralized with triethylamine.

Meanwhile, 2.24 g (0.005 M) of $$\text{H-Cys-O}^t\text{Bu} \overset{\text{PMB}}{|}$$

L-tartrate is dissolved in dimethylformamide and the solution is neutralized with 1.4 ml of triethylamine under ice-cooling. This solution is combined with the azide solution prepared as above and the combined solution is stirred at 4° C. for 48 hours. Insolubles are removed by filtration and the filtrate is concentrated. Water is added to the residue and the resulting powder is collected by filtration. The powder is recrystallized twice from methanol.

Yield: 3.55 g (77.7%). m.p.: 193.0°–195.0° C. (decomp.)
$[\alpha]_D^{25} -18.0°$ (c=0.56, dimethylformamide)
Elemental analysis: Calcd. for $C_{43}H_{56}O_{14}N_6S$: C, 56.57; H, 6.18; N, 9.21; S, 3.51. Found C, 56.31; H, 6.08; N, 9.34; S, 3.47.

(8) Synthesis of Z(NO₂)-Trp-OH

The compound is prepared by a conventional procedure.
Yield: 88.6% m.p.: 108.0°–115.0° C. (decomp.)
$[\alpha]_D^{23} -43.5°$ C. (c=0.65, dimethylformamide)
Elemental analysis: Calcd. for $C_{19}H_{17}O_4N_3 \cdot 2H_2O$: C, 58.91; H, 5.46; N, 10.85. Found C, 59.63; H, 4.63; N, 10.74.

$$\text{Synthesis of Z(NO}_2\text{)-Trp-Lys-OH . DCHA} \overset{\text{BOC}}{|} \quad (9)$$

In 100 ml of dimethylformamide is dissolved 7.39 g (0.03 M) of $$\text{H-Lys-OH,} \overset{\text{BOC}}{|}$$

followed by addition of 4.2 ml (0.03 M) of triethylamine. To the solution is added Z(NO₂)-Trp-ONB which is prepared from 10.5 g (0.03 M) of Z(NO₂)-Trp-OH, 5.4 g (0.03 M) of HONB and 6.19 g (0.03 M) of dicyclohexylcarbodiimide. The mixture is stirred at room temperature for 12 hours and the solvent is distilled off. After addition of 30 ml of 1N HCl, the mixture is dissolved in ethyl acetate. The ethyl acetate layer is washed three times with water, dried and distilled to evaporate the solvent. The oily residue is dissolved in 100 ml of acetonitrile and 6.0 ml (0.03 M) of dicyclohexylamine is added and the mixture is left standing in a refrigerator. Resulting gelatinous crystals are collected by filtration and recrystallized from acetonitrile.

Yield: 12.5 g (52.6%) m.p.: 95.0°–100.0° C.
$[\alpha]_D^{25} -20.9°$ (c=0.56, dimethylformamide)
Elemental analysis: Calcd. for $C_{30}H_{37}O_9N_5 \cdot C_{12}H_{23}N$: C, 63.61; H, 7.63; N, 10.60. Found C, 63.77; H, 7.67; N, 11.08.

$$\text{Synthesis of Z(NO}_2\text{)-Trp-Lys-Thr-Phe-Thr-Ser-Cys-O}^t\text{Bu} \overset{\text{BOC} \quad \text{PMB}}{| \quad\quad |} \quad (10)$$

In 150 ml of a mixture of acetic acid and water (8:2 by volume), is dissolved 3.29 g (0.0036 M) of $$\text{Z(NO}_2\text{)-Thr-Phe-Thr-Ser-Cys-O}^t\text{Bu} \overset{\text{PMB}}{|}$$

and the solution is subjected to catalytic reduction at 50° C. for 8 hours in the presence of palladium black. The catalyst is removed by filtration and the filtrate is lyophilized. The lyophilizate is dissolved in methanol and ether is added. Resulting precipitate is collected by filtration and reprecipitated from methanol-ether. Yield: 2.75 g In a small amount of dimethylformamide is dissolved 2.62 g (0.0033 M) of the powder obtained above. A solution of 627 mg of p-toluenesulfonic acid in dimethylformamide is added to the solution under cooling and the mixture is left standing. Most of the dimethylformamide is distilled off and ether is added to the residue. Resulting powder is collected by filtration and dissolved in 20 ml of dimethylformamide, followed by addition of

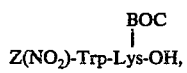
Z(NO₂)-Trp-Lys-OH, which is prepared from 2.88 g (0.0036 M) of

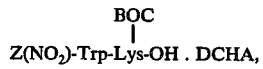
Z(NO₂)-Trp-Lys-OH . DCHA, and further addition of 1.30 g (0.0072 M) of HONB, 0.42 ml (0.0033 M) of N-ethylmorpholine and dicyclohexylcarbodiimide 819 mg (0.004 M). The mixture is stirred at −10° C. for 3 hours and further stirred at room temperature for 48 hours. Resulting dicyclohexylurea is removed by filtration and the filtrate is concentrated. Water is added to the residue.

Resulting precipitate is collected by filtration and recrystallized twice from methanol.

Yield: 3.5 g (80.6%) m.p.: 183.0°–185.0° C. (decomp.) $[\alpha]_D^{25} -26.6°$ (c=0.67, dimethylformamide)

Elemental analysis: Calcd. for $C_{64}H_{84}O_{18}N_{10}S$: C, 58.52; H, 6.45; N, 10.66; S, 2.44. Found C, 58.36; H, 6.47; N, 10.49; S, 2.54.

(11) Synthesis of Z-Phe-Phe-O'Bu

According to a conventional procedure, 17.8 g (0.05 M) of Z-Phe-O'Bu is catalytically reduced in methanol to H-Phe-O'Bu. To this is added a solution of Z-Phe-ONB which is prepared from 15.0 g (0.05 M) of Z-Phe-OH, 9.0 g (0.05 M) of HONB and 10.3 g (0.05 M) of dicyclohexylcarbodiimide, and the mixture is stirred at room temperature for 12 hours. The dioxane is distilled off and the residue is dissolved in ethyl acetate. The solution is washed in a conventional manner, dried and distilled to evaporate the ethyl acetate. Resulting crystals are collected by filtration and recrystallized from ethyl acetate.

Yield: 15.4 g (60.0%) m.p.: 107.0°–109.0° C. $[\alpha]_D^{27} -13.5°$ (c=0.53, dimethylformamide)

Elemental analysis: Calcd. for $C_{30}H_{34}O_5N_2$: C, 71.96; H, 6.82; N, 5.57. Found C, 71.61; H, 6.64; N, 5.50.

(12) Synthesis of BOC-Asn-Phe-Phe-O'Bu

In a conventional procedure, 13.1 g (0.026 M) of Z-Phe-Phe-O'Bu is catalytically reduced in methanol to H-Phe-Phe-O'Bu. This is dissolved in 50 ml of dimethylformamide together with 6.04 g (0.026 M) of BOC-Asn-OH and 4.65 g (0.026 M) of HONB. Under ice-cooling, 5.36 g (0.026 M) of dicyclohexylcarbodiimide is added and the mixture is stirred at 0° C. for 3 hours and at room temperature for further 12 hours. Resulting dicyclohexylurea is removed by filtration and the filtrate is concentrated in vacuo, followed by addition of water. Resulting crystals are collected by filtration and recrystallized twice from methanol.

Yield: 11.0 g (72.8%). m.p.: 163.0°–166.0° C. $[\alpha]_D^{27} -28.9°$ (c=0.85, dimethylformamide)

Elemental analysis: Calcd. for $C_{31}H_{42}O_7N_4$: C, 63.90; H, 7.27; N, 9.62. Found C, 64.12; H, 7.20; N, 9.90.

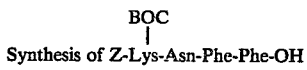
Synthesis of Z-Lys-Asn-Phe-Phe-OH (13)

In 100 ml of trifluoroacetic acid is dissolved 10.5 g (0.018 M) of BOC-Asn-Phe-Phe-O'Bu and the mixture is left standing at room temperature for 1.5 hours. The trifluoroacetic acid is distilled off under reduced pressure and ether is added to the residue. Resulting precipitate is collected by filtration and dried and dissolved in 100 ml of dimethylformamide. To the solution is added 5.04 ml (0.036 M) of triethylamine and a solution of

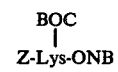
Z-Lys-ONB which is prepared from 8.2 g (0.0216 M) of

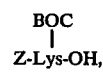
Z-Lys-OH, 3.8 g (0.0216 M) of HONB and 4.4 g (0.0216 M) of dicyclohexylcarbodiimide. The mixture is stirred at room temperature for 12 hours, followed by addition of 10 ml of acetic acid. The solvent is distilled off in vacuo and water is added to the residue. Resulting precipitate is collected by filtration and purified by reprecipitating twice from aqueous methanol and then from dimethylformamide-ethyl acetate.

Yield: 11.1 g (78.1%) m.p.: 194.0°–196.0° C. (decomp.)

$[\alpha]_D^{27} -26.9°$ (c=0.59, dimethylformamide)

Elemental analysis: Calcd. for $C_{41}H_{52}O_{10}N_6$: C, 62.42; H, 6.64; N, 10.65. Found C, 62.27; H, 6.66; N, 10.72.

Synthesis of Z(NO₂)-Cys-OH (14)

The compound is prepared by a conventional procedure.

Yield: 80.0% m.p.: 163.0°–165.0° C. $[\alpha]_D^{23} -51.2°$ (c=0.61, dimethylformamide)

Elemental analysis: Calcd. for $C_{19}H_{20}O_7N_2S$: C, 54.28; H, 4.79; N, 6.66; S, 7.62. Found C, 54.18; H, 4.74; N, 6.57; S, 7.56

Synthesis of Z(NO₂)-Cys-Lys-Asn-Phe-Phe-OH (15)

According to a conventional procedure, 10.3 g (0.013 M) of

Z-Lys-Asn-Phe-Phe-OH is catalytically reduced in a mixture of acetic acid and water (8:2 by volume). Resulting

H-Lys-Asn-Phe-Phe-OH is purified by two times of reprecipitation from ethanol.

Yield: 7.0 g

In 100 ml of dimethylformamide is suspended 6.55 g (0.01 M) of the compound, followed by addition of 1.40 ml (0.01 M) of triethylamine and further addition of a solution of dimethylformamide in PMB
|
Z(NO₂)-Cys-ONB which is prepared from 5.05 g (0.012 M) of PMB
|
Z(NO₂)-Cys-OH, 2.15 g (0.012 M) of HONB and 2.48 g (0.012 M) of dicyclohexylcarbodiimide. The mixture is stirred at room temperature for 12 hours. After addition of 10 ml of acetic acid, the dimethylformamide is distilled off in vacuo and water is added to the residue. Resulting precipitate is collected by filtration and recrystallized twice from a mixture of methanol and water (8:2 by volume)

Yield: 9.6 g (92.3%) m.p.: 209.0°–210.0° C. (decomp.) $[\alpha]_D^{27}$ −24.6° (c=0.74, dimethylformamide)

Elemental analysis: Calcd. for $C_{52}H_{64}O_{14}N_8S$: C, 59.08; H, 6.10; N, 10.60; S, 3.03. Found C, 59.04; H, 6.02; N, 10.60; S, 3.19.

(16) Synthesis of BOC-Ala-Gly-OBzl

In 50 ml of dimethylformamide is dissolved 8.10 g (0.024 M) of H-Gly-OBzl.p-Ts-OH and under ice-cooling 3.36 ml (0.024 M) of triethylamine is added. To this is added BOC-Ala-ONB which is prepared from 4.35 g (0.023 M) of BOC-Ala-OH, 4.12 g (0.023 M) of HONB and 4.74 g (0.023 M) of dicyclohexylcarbodiimide. The mixture is stirred at room temperature for 12 hours and distilled off in vacuo. The residue is dissolved in ethyl acetate, washed in a conventional manner and dried. The ethyl acetate is distilled off and petroleum ether is added to the residue to crystallize it. The crystals are collected by filtration and recrystallized from ethyl acetate-petroleum benzin.

Yield: 5.5 g (71.2%) m.p.: 86.0°–87.0° C. $[\alpha]_D^{27}$ −10.8° (c=0.56, dimethylformamide)

Elemental analysis: Calcd. for $C_{17}H_{24}O_5N_2$: C, 60.70; H, 7.19; N, 8.33. Found C, 60.82; H, 7.19; N, 8.28.

(17) Synthesis of BOC-Ala-Gly-OH

According to a conventional procedure, the compound is produced by reducing catalytically 5.29 g (0.015 M) of BOC-Ala-Gly-OBzl in methanol.

Yield: 3.3 g (85.3%) m.p.: 111.0°–113.0° C. (decomp.) $[\alpha]_D^{27}$ −6.8° (c=0.56, dimethylformamide)

Elemental analysis: Calcd. for $C_{10}H_{18}O_5N_2·1/2H_2O$: C, 47.05; H, 7.50; N, 10.98. Found C, 46.66; H, 7.65; N, 11.03.

(18)

PMB BOC
 |   |
Synthesis of BOC-Ala-Gly-Cys-Lys-Asn-Phe-Phe-OH

In a mixture of acetic acid and water (8:2 by volume), 5.2 g (0.005 M) of

PMB BOC
 |   |
Z(NO₂)-Cys-Lys-Asn-Phe-Phe-OH is catalytically reduced on palladium black at 50° C. for 8 hours. The catalyst is removed by filtration and the filtrate is concentrated and the residue is triturated with ether. The resulting powder is collected by filtration and reprecipitated from ethanol.

Yield: 4.05 g

The powder is suspended in 50 ml of dimethylformamide, followed by addition of 0.7 ml of triethylamine and further addition of BOC-Ala-Gly-ONB which is prepared from 1.48 g (0.006 M) of BOC-Ala-Gly-OH, 1.08 g (0.006 M) of HONB and 1.24 g (0.006 M) of dicyclohexylcarbodiimide. The mixture is vigorously stirred for 12 hours. After being acidified with 10 ml of acetic acid, the dimethylformamide is distilled off in vacuo. Water is added to the residue, and the resulting powder is collected by filtration and reprecipitated twice from a mixture of methanol and water (8:2 by volume).

Yield 3.5 g (60.4%) m.p.: 201.0°–203.0° C. (decomp.) $[\alpha]_D^{25}$ −28.2° (c=0.69, dimethylformamide)

Elemental analysis: Calcd. for $C_{54}H_{75}O_{14}N_9S$: C, 58.63; H, 6.83; N, 11.40; S, 2.90. Found C, 58.86; H, 6.83; N, 11.53; S, 2.79.

(19)

PMB BOC       BOC           PMB
 |   |         |             |
Synthesis of BOC-Ala-Gly-Cys-Lys-Asn-Phe-Phe-Trp-Lys-Thr-Phe-Thr-Ser-Cys-OᵗBu In 150 ml of a mixture of acetic acid and water (8:2 by volume) is suspended 3.29 g (0.0025 M) of BOC           PMB
 |             |
Z(NO₂)-Trp-Lys-Thr-Phe-Thr-Ser-Cys-OᵗBu and the compound is catalytically reduced on palladium black at 50° C. for 5 hours. The catalyst is removed by filtration and the filtrate is concentrated under reduced pressure. A small amount of ethanol is added to the residue and ether is further added to triturate the residue. This procedure is repeated.

Yield: 2.90 g

In a small amount of dimethylformamide is dissolved 2.69 g (0.0023 M) of the compound prepared above, and under ice-cooling a solution of 437 mg (0.0023 M) of p-toluenesulfonic acid in dimethylformamide is added dropwise. After the mixture is left standing for a while, the solvent is distilled off in vacuo and ether is added to triturate the residue. Resulting powder is dissolved in 20 ml of dimethylformamide, followed by addition of 823 mg (0.0046 M) of HONB, 0.29 ml (0.0023 M) of N-ethylmorpholine and 2.54 g (0.0023 M) of PMB BOC
 |   |
BOC-Ala-Gly-Cys-Lys-Asn-Phe-Phe-OH.

At −10° C., 949 mg (0.0046 M) of dicyclohexylcarbodiimide in dimethylformamide is added and the mixture is stirred for 3 hours and for further 72 hours at room temperature. Resulting dicyclohexylurea is removed by filtration and the filtrate is concentrated in vacuo. Water is added to the residue, and resulting precipitate is collected by filtration and reprecipitated twice from methanol.

Yield: 3.8 g (75.1%) m.p.: 224.0°–226.0° C. (decomp.)
$[\alpha]_D^{25}$ −18.3° (c=0.70, dimethylformamide)
Elemental analysis: Calcd. for $C_{109}H_{154}O_{26}N_{18}S_2$: C, 59.62; H, 7.06; N, 11.47; S, 2.92. Found C, 59.55; H, 6.75; N, 11.32; S, 2.95.

dissolved in a small amount of water. The solution is passed through a column (2.0 × 7.0 cm) of Amberlite IRA-140 (acetate form) to effect ion exchange. The effluent of 60 ml is passed through a column (5.5 × 35.0 cm) of Sephadex LH-20, which is eluted with 0.1 N acetic acid solution. Major fractions of 560–640 ml are collected and lyophilized.

(20)

Synthesis of H-Ala-Gly-Cys-Lys-Asn-Phe-Phe-Trp-Lys-Thr-Phe-Thr-Ser-Cys-OH (somatostatin)

In 20 ml of a mixture of acetic acid and water (8:2 by volume) is dissolved 220 mg (0.1 mM) of

BOC-Ala-Gly-Cys-Lys-Asn-Phe-Phe-Trp-Lys-Thr-Phe-Thr-Ser-Cys-O$^t$Bu.

To the solution is added 171 mg (0.4 mM) of Hg(CF$_3$COO)$_2$ and the mixture is stirred at room temperature for 12 hours. Hydrogen sulfide gas is bubbled into the reaction mixture and resulting black precipitate is removed by filtration with celite. The filtrate is concentrated under reduced pressure and the residue is triturated with ether containing a minor amount of β-mercaptoethanol. Resulting powder is collected by filtration and dried. Yield: 193 mg.

The compound is dissolved in 500 ml of dimethylformamide, followed by addition of 0.28 ml of 10% triethylamine-dimethylformamide and further addition of 30 mg of 1,2-diiodoethane. The reaction mixture is stirred at room temperature for 30 minutes and the solvent is distilled off in vacuo. The residue is trifurated with ether and resulting powder is collected by filtration and dried.

Yield: 158 mg

The compound is dissolved in 3 ml of a mixture of trifluoroacetic acid and water (9:1 by volume) and the solution is shaken at room temperature for 30 minutes. The trifluoroacetic acid is distilled off below 30° C. under reduced pressure for 10 minutes. Ether is added, and resulting precipitate is collected by filtration and Yield: 20.4 mg
$[\alpha]_D^{26}$ −31.2° (c=0.13, 1% acetic acid)

Thin layer chromatography: Rf=0.60 (n-butanol:pyridine:acetic acid:water=30:20:6:24 by volume, Avicel), Rf=0.40 (n-butanol:ethyl acetate:acetic acid:water=1:1:1:1 by volume, silica gel)

Amino acid analysis (6N HCl, 110° C., 24 hours) Lys, 1.97(2); Asp, 1.01(1), Thr, 1.95(2); Ser, 0.92(1); Gly, 1.00(1); Ala, 1.02(1); Half Cys, 1.58(2); Phe, 3.01(3), average recovery 82%.

What is claimed is:

1. A method for removing the S-protecting group from an amino acid or peptide having a thiol group protected with a p-mertoxybenzyl, 1-adamantyl or t-butyl group, comprising reacting the protected amino acid or peptide with the mercuric salt of acetic acid in a member selected from the group consisting of trifluoroacetic acid and the mercuric salt of trichloro- or trifluoroacetic acid in acetic acid to thereby substitute the protective group with mercury and remove the mercury from the amino acid or peptide.

2. A method as claimed in claim 1, wherein the amino acid is cysteine.

3. A method as claimed in claim 1, wherein the peptide has residue(s) of cysteine.

* * * * *

UNITED STATES PATENT OFFICE
CERTIFICATE OF CORRECTION

Patent No. 4,111,924  Dated September 5, 1978

Inventor(s) Masahiko Fujino, et al.

It is certified that error appears in the above-identified patent and that said Letters Patent are hereby corrected as shown below:

Column 1, line 23: Change "1965" to --1935--.

Column 18, line 30: Change "p-mertoxybenzyl" to

--p-methoxybenzyl--.

Signed and Sealed this

Fifth Day of June 1979

[SEAL]

Attest:

RUTH C. MASON
Attesting Officer

DONALD W. BANNER
Commissioner of Patents and Trademarks